(12) United States Patent
Miller et al.

(10) Patent No.: US 8,927,771 B2
(45) Date of Patent: Jan. 6, 2015

(54) PHARMACEUTICALLY ACCEPTABLE COCRYSTALS OF N-[2-(7-METHOXYL-1-NAPHTYL)ETHYL]ACETAMIDE AND METHODS OF THEIR PREPARATION

(75) Inventors: Gary James Miller, Glasgow (GB); Ludek Ridvan, Prague (CZ); Jindrich Richter, Pardubice (CZ); Ondrej Dammer, Dobriv (CZ); Tomas Chvojka, Podebrady (CZ); Tomas Pekarek, Prague (CZ); Winfried Heyse, Mörfelden-Walldorf (DE); Norbert Nagel, Mörfelden-Walldorf (DE)

(73) Assignee: Zentiva k.s., Prague (CZ)

( * ) Notice: Subject to any disclaimer, the term of this patent is extended or adjusted under 35 U.S.C. 154(b) by 0 days.

(21) Appl. No.: 14/114,211

(22) PCT Filed: Apr. 25, 2012

(86) PCT No.: PCT/EP2012/001761
§ 371 (c)(1),
(2), (4) Date: Oct. 27, 2013

(87) PCT Pub. No.: WO2012/146371
PCT Pub. Date: Nov. 1, 2012

(65) Prior Publication Data
US 2014/0051887 A1 Feb. 20, 2014

(30) Foreign Application Priority Data
Apr. 28, 2011 (EP) .................................... 11075073

(51) Int. Cl.
| C07C 233/25 | (2006.01) |
| C07C 309/20 | (2006.01) |
| C07C 231/22 | (2006.01) |
| C07C 309/29 | (2006.01) |
| C07C 233/18 | (2006.01) |
| C07C 57/145 | (2006.01) |
| C07C 59/265 | (2006.01) |

(52) U.S. Cl.
CPC ............. C07C 233/25 (2013.01); C07C 309/29 (2013.01); C07C 233/18 (2013.01); C07C 231/22 (2013.01); C07C 57/145 (2013.01); C07B 2200/13 (2013.01); C07C 59/265 (2013.01)
USPC ......................................................... 564/219

(58) Field of Classification Search
CPC ............................ C07C 233/25; C07C 231/22
USPC .......................................................... 564/219
See application file for complete search history.

(56) References Cited

U.S. PATENT DOCUMENTS
8,710,101 B2 * 4/2014 Letellier et al. ............... 514/630

FOREIGN PATENT DOCUMENTS
| WO | WO 2004/078163 | 9/2004 |
| WO | WO 2005/002562 | 1/2005 |
| WO | WO 2008/035177 | 3/2008 |
| WO | WO 2011/079609 | 7/2011 |
| WO | WO 2012/046253 | 4/2012 |

OTHER PUBLICATIONS

International Search Report mailed on Sep. 17, 2012 for International Application No. PCT/EP2012/001761.
Zheng et al., Structures of Polymorphic Agomelatine and Its Cocrystals with Acetic Acid and Ethylene Glycol, Crystal Growth & Design, vol. 11, No. 2, pp. 466-471, 2011, XP 002658583.
Aakeröy and Salmon, Building co-crystals with molecular sense and supermolecular sensibility, Cryst. Eng. Comm., vol. 7, No. 72, pp. 439-448, 2005.

* cited by examiner

*Primary Examiner* — Shailendra Kumar
(74) *Attorney, Agent, or Firm* — Pearl Cohen Zedek Latzer Baratz LLP

(57) ABSTRACT

The present invention relates to novel solid forms of agomelatine (I), specifically novel phaamaceutically acceptable cocrystals thereof, as well as to methods of preparing them. Three pharmaceutically acceptable cocrystals of (I) that have physico-chemical properties acceptable for pharmaceutical development were obtained.

(I)

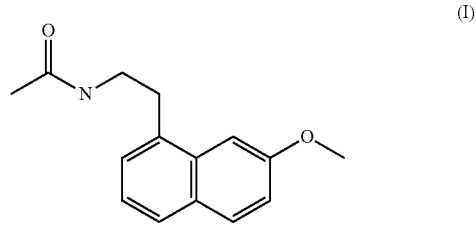

5 Claims, 12 Drawing Sheets

Figure 1:
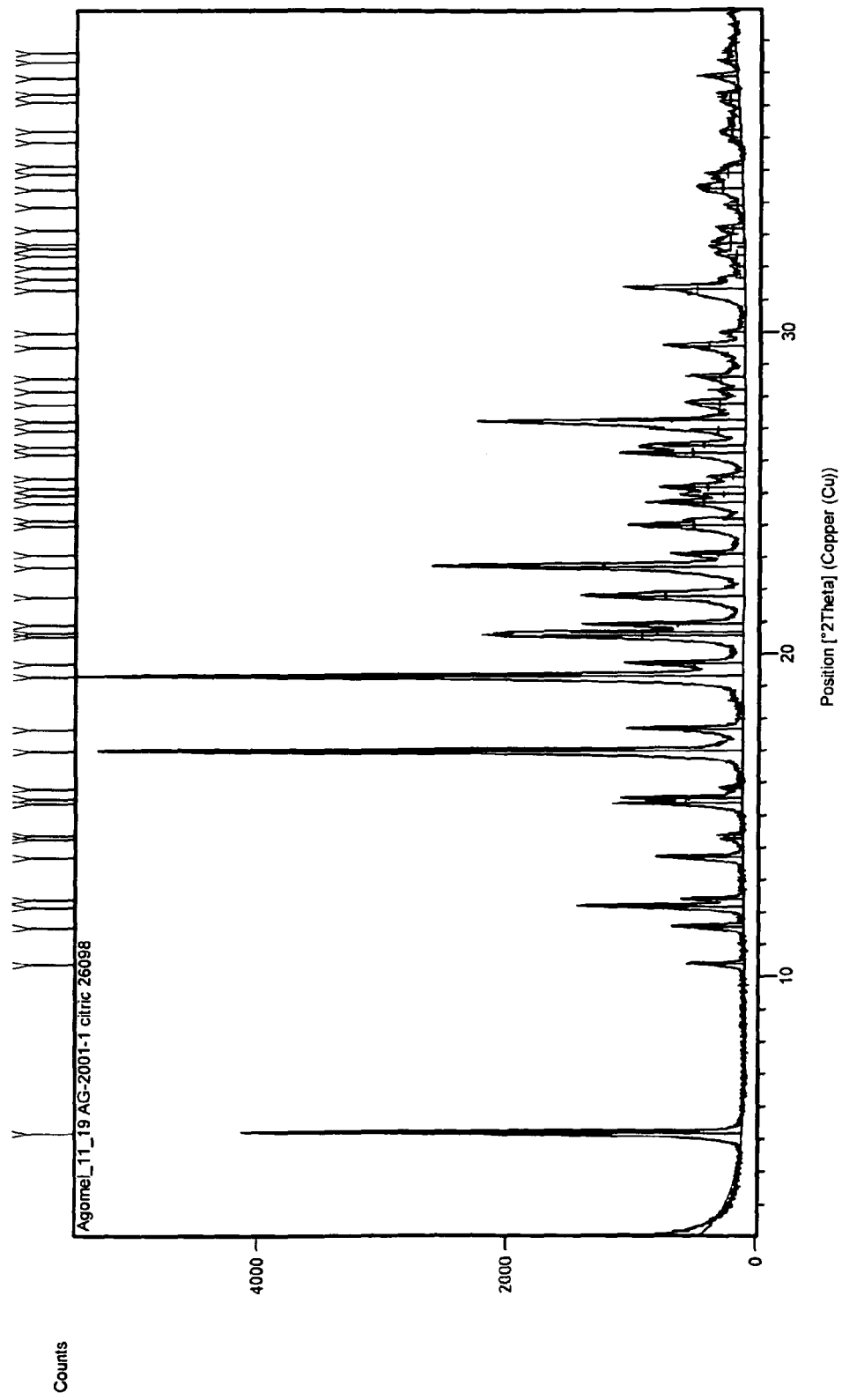

PHARMACEUTICALLY ACCEPTABLE COCRYSTALS OF N-[2-(7-METHOXYL-1-NAPHTYL)ETHYL]ACETAMIDE AND METHODS OF THEIR PREPARATION

CROSS-REFERENCE TO RELATED APPLICATIONS

This application is a National Phase Application of PCT International Application No. PCT/EP2012/001761, filed on Apr. 25, 2012, claiming the benefit of European Patent Application No. 11075073.4, filed Apr. 28, 2011, which are hereby incorporated by reference.

TECHNICAL FIELD

The present invention relates to novel solid forms of agomelatine, specifically novel pharmaceutically acceptable cocrystals thereof, as well as to methods of preparing them.

BACKGROUND ART

N-[2-(7-Methoxy-1-naphthyl)ethyl]acetamide, also known as agomelatine, of formula I

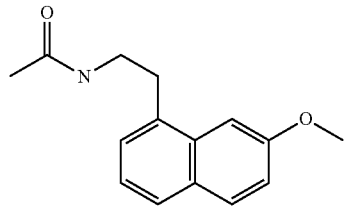

(I)

is a melatogenic agonist of melatonin receptor 1 (MT-1) and melatonin receptor 2 (MT-2) and a 5-HT2C antagonist that is licensed as a treatment for depression or major depressive disorder.

The physicochemical properties endowed by the solid-state structure is a critical parameter in the development of solid dosage forms of pharmaceuticals as these properties can affect the bioavailability, stability and processability of the active pharmaceutical ingredient. It is known that a solid active pharmaceutical ingredient can potentially exist in both amorphous and crystalline forms. It is further known that for a crystalline solid various polymorphs and solvates are possible.

Polymorphism arises from the crystallisation of a substance in more than one crystalline form, each form being identical in terms of the chemical composition of the system but differing in the arrangement of molecules in the crystal lattice. It is also possible for solvent molecules to become included in the crystal structure in addition to the active pharmaceutical molecules to produce a crystalline solvate or, when the solvent is specifically water, a crystalline hydrate. It is an accepted principle that different polymorphs, solvates or hydrates of an active pharmaceutical molecule may have different physicochemical properties as a result of the differences in the number, type and strength of intermolecular interactions between the molecules in the different crystalline forms. For example, different polymorphs and solvates have been shown to differ in their solubilities, stabilities, hygroscopicities and different mechanical properties relating to qualities such as their filterability and flowability.

For active pharmaceutical molecules containing an acidic or basic functional group this principle can be exploited by the preparation of various crystalline salts of the active pharmaceutical ingredient to modulate and optimize the physicochemical properties of the obtained crystalline solid for a specific application. The changes in the physicochemical properties resulting from the inclusion of a counterion in the crystal structure are a consequence of both the molecular structure and properties of the active pharmaceutical molecule and counterion and the intermolecular interactions between the molecules in the crystal structure. It is therefore possible to change the physicochemical properties of the crystalline solid through the inclusion of different counterions, giving crystalline salts with different physicochemical properties. This is a well-established and important technique in pharmaceutical development and is standard practice in the development of new solid forms of active pharmaceutical ingredients (API).

Typical counterions used in pharmaceutical salt formation are acidic or basic molecules or ions that are considered to be pharmaceutically acceptable due to their low toxicity, well established use as food additives or their natural occurrence in the human organism. Typical examples of counterions used include carboxylic acids, sulfonic acids, hydroxy acids, amino acids and inorganic acids for basic active pharmaceutical molecules and amines, alkali metals, alkaline metals and amino acids for acidic active pharmaceutical substances.

A major limitation of salt formation is that it is inapplicable to neutral APIs. Furthermore, the range of possible counterions for weakly acidic or weakly basic APIs can be limited by the ionization constant of the acid or base groups on the molecule. Finally, it has been demonstrated that the composition of crystalline molecular salts can be highly unpredictable, particularly with regards to hydrate and solvate formation.

Faced with these limitations, the formation of pharmaceutically acceptable cocrystals of active pharmaceutical molecules offers an alternative approach to the generation of new solid forms of the active substance. In this context a cocrystal, or alternatively co-crystal, is understood to be a binary molecular crystal containing the molecules of the API together with another molecular species in a defined stoichiometric ratio where both components are in their neutral state. In this case the terms "cocrystal" and "co-crystal" are generally understood to be synonymous terms referring to such a system. The second component in the cocrystal (the component other than the active pharmaceutical ingredient) is commonly referred to as a "cocrystal former". Pharmaceutically acceptable cocrystal formers include any molecule considered acceptable as a counterion for a pharmaceutical salt or known as a pharmaceutical excipient.

A widely accepted definition of a pharmaceutical cocrystal is a crystalline system containing an active pharmaceutical molecule and a cocrystal former that is a solid at ambient temperature and pressure in a defined stoichiometric ratio, although a cocrystal is not limited to containing only two components. The components of the cocrystal are linked by hydrogen bonding and other non-covalent and non-ionic interactions. (Aakeroy and Salmon, CrystEngComm, 2005, 439-448). This definition distinguishes cocrystals from crystalline solvates, in which case one of the components is a liquid at ambient temperature and pressure.

It is also understood that, in common with single-component crystalline systems and salts, cocrystals can also contain solvent molecules or water to form cocrystal solvates or hydrates. It is further understood that, in common with all other types of crystalline system, cocrystals are capable of existing as different packing arrangements of the same molecular components to give polymorphic forms of a particular cocrystal.

In common with other types of crystalline system, particularly crystalline salts, it is currently impossible to predict ab initio which combination of active pharmaceutical compound and cocrystal former will crystallize as a cocrystal or its crystal structure. Furthermore it is impossible to predict the physicochemical properties of a cocrystal either from the molecular structures of the component molecules or from the crystal structure of the cocrystal if this is known. As a result the discovery and selection of an appropriate cocrystal form of an active pharmaceutical compound to satisfy particular physicochemical property requirements is a non-trivial process and the ideal cocrystal form is not obvious from the outset.

N-[2-(7-Methoxy-1-naphthyl)ethyl]acetamide is classified as a high solubility drug in accordance with the BCS classification system and a criteria for the selection of a suitable cocrystal form will be that it displays bioequivalence to the marketed single component form of N-[2-(7-Methoxy-1-naphthyl)ethyl]acetamide. A new cocrystal, as for a new polymorph, salt or hydrate, may be endowed with physicochemical properties that offer an advantage over the current marketed solid form if the new cocrystal shows superior stability of the chemical or solid form under storage conditions, reproducibility and purity of the solid form obtained to ensure consistency in the efficacy of the drug product manufactured or mechanical properties or physical characteristics that improve the processability and manufacturability of the solid form.

The identification of crystalline forms may be a non-trivial process and the use of complementary techniques including X-Ray powder diffraction (XRPD), differential scanning calorimetry (DSC) and vibrational spectroscopy (for example Raman spectroscopy) is advisable to clearly and unambiguously identify the crystalline form obtained. X-ray powder diffraction is the routine method for unambiguously characterising crystalline phases and, after suitable calibration, assessing phase purity. Single-crystal X-ray diffraction is the optimum method for characterizing a crystalline solid, enabling the determination of the crystallographic unit cell and the chemical identity, molecular conformation and stoichiometry of the molecules in the crystal structure and their intermolecular interactions. However, its requirement for relatively large and high-quality single crystals restricts the use of this technique to systems capable of producing suitable crystalline material and hence this is not a routinely employed method.

A recent paper (Crystal Growth and Design, 2011, pages 466-471) described two binary crystalline systems containing agomelatine with acetic acid and ethylene glycol. Given that both ethylene glycol and acetic acid are liquids at ambient temperature and pressure the two systems described do not meet the criteria for cocrystals given above and are arguably solvates. In any case, both these systems have drawbacks for use in a pharmaceutical formulation. Ethylene glycol is not considered to be pharmaceutically acceptable. Whilst acetic acid is pharmaceutically acceptable the crystallisation of the system in the article was performed by slow vapor diffusion. Although this is a sensible method for the laboratory-scale crystallization of diffraction-quality single crystals it is not practicable for the crystallisation of the quantities of material routinely required for pharmaceutical production. Moreover, their melting points are low enough to risk problems in pharmaceutical manufacturing. Therefore the development of other stable pharmaceutically acceptable cocrystals that can be obtained robustly and reproducibly using scalable crystallisation procedures is highly desirable.

DESCRIPTION OF THE INVENTION

The present invention relates to new solid forms of N-[2-(7-Methoxy-1-naphthyl)ethyl]acetamide in the form of stable cocrystals with pharmaceutically acceptable organic acids possessing two or more carboxylic acid groups or at least one sulfonic acid group. By definition a cocrystal must contain the two components in a uniform stoichiometric ratio throughout the crystalline lattice; however different polymorphs of a cocrystal can contain the two components in different molar ratios. Polymorphic cocrystals could contain any molar ratio of agomelatin to cocrystal former but would typically be in the range of 3:1 to 1:3. It has surprisingly been found that, according to this invention, the preferred and most suitable stoichiometric ratio is 1:1, irrespective of the number of functional groups present on the cocrystal former. The present invention further relates to methods of preparation of cocrystals according to the invention. The cocrystals according to the invention represent a reservoir of highly consistent and stable forms of agomelatine from which the form with the most suitable physicochemical and pharmaceutical as well as pharmacokinetic properties can be chosen for a particular pharmaceutical use.

In particular this invention relates to substantially pure crystalline forms of the active pharmaceutical ingredient N-[2-(7-methoxy-1-naphthyl)ethyl]acetamide as pharmaceutically acceptable cocrystals, methods of preparing these cocrystals and to the use of said cocrystals in the preparation of pharmaceutical formulations for the treatment of depression or major depressive disorder. More particularly, these cocrystals can be prepared reproducibly and have bioavailability, stability, hygroscopicity and mechanical properties that make them suitable for use in the preparation of pharmaceutical formulations that can satisfy the regulations in force governing the quality of pharmaceutical preparations.

The expression "substantially pure crystalline form" as used herein means a crystalline form characterized by XRPD that contains no more than traces of the signals relating to other crystalline forms. Preferably, the presence of such signals is equal to or below the limit of detection (LOD) of the method used and therefore, in the majority of the cases described herein, the expression "substantially pure crystalline form" means a crystalline form with a purity of at least 90%. The term "main peaks" used herein means peaks with a relative intensity >3%.

The preferred embodiment of the invention is the citric acid cocrystal of N-[2-(7-Methoxy-1-naphthyl)ethyl]acetamide, having the empirical formula $C_{15} H_{17} N O_2 . C_6 H_8 O_7$, characterised at ambient conditions by a monoclinic system in space group $P2_1/c$ with cell parameters a=7.843 (1) Å, b=33.852 (2) Å, c=8.288 (1) Å, α=90°, β=109.40°, γ=90°, V=2075.5 (2) Å$^3$ with the experimental XRPD pattern given in FIG. 1 and comprising the main peaks listed in Table 1. The three-dimensional structure of this cocrystal obtained by single-crystal X-ray diffraction (SXRD) is given in FIG 1*a* and the calculated XRPD pattern calculated from the single crystal structure is in good agreement with the experimental diffraction pattern as shown in FIG. 1*b*.

TABLE 1

Table of diffraction peaks for agomelatin cocrystal with citric acid.

| Diffraction angle (°2θ) | d-spacing [Å] | Relative intensity (%) |
|---|---|---|
| 5.18 | 17.033 | 71.9 |
| 10.40 | 8.497 | 8.7 |
| 11.55 | 7.656 | 10.6 |
| 12.19 | 7.256 | 26.2 |
| 13.70 | 6.457 | 14.2 |
| 15.38 | 5.757 | 18.0 |
| 15.54 | 5.697 | 17.1 |
| 16.99 | 5.213 | 96.6 |
| 17.68 | 5.012 | 16.7 |
| 19.31 | 4.592 | 100.0 |
| 19.72 | 4.498 | 15.3 |
| 20.57 | 4.314 | 32.6 |
| 20.93 | 4.241 | 21.3 |
| 21.81 | 4.072 | 25.0 |
| 22.73 | 3.909 | 45.5 |
| 24.00 | 3.706 | 16.3 |
| 24.71 | 3.601 | 12.9 |
| 25.18 | 3.534 | 11.9 |
| 26.25 | 3.393 | 16.7 |
| 26.48 | 3.363 | 13.1 |
| 27.25 | 3.270 | 23.9 |
| 27.78 | 3.209 | 8.3 |
| 28.59 | 3.120 | 7.9 |
| 29.56 | 3.020 | 11.6 |
| 31.34 | 2.852 | 15.4 |
| 34.45 | 2.602 | 6.5 |
| 37.89 | 2.373 | 5.1 |

Figure 2:
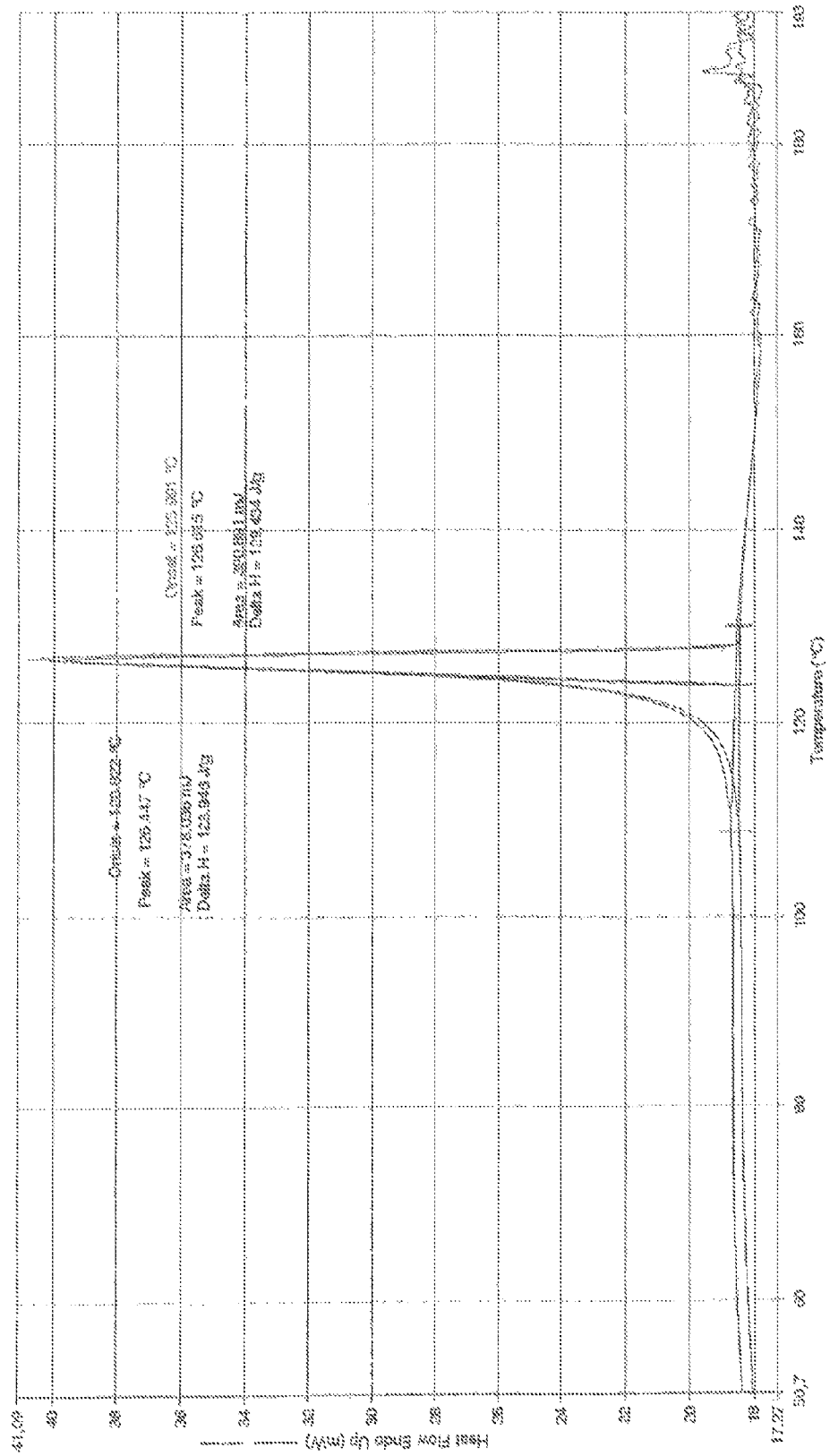

This citric acid cocrystal of N-[2-(7-Methoxy-1-naphthyl)ethyl]acetamide is further characterized by the differential scanning calorimetry (DSC) thermograph shown in FIG. 2. which shows an endothermic event corresponding to a melt with an onset temperature of approximately 124° C. The melting point is therefore approximately 18° C. higher than the pure Form I polymorph of N-[2-(7-Methoxy-1-naphthyl)ethyl]acetamide. The melting point of a drug substance can affect its compatibility with production and formulation equipment, with lower melting solids being more likely to melt onto equipment during routine processes such as milling and grinding. Therefore, a higher melting form of a drug substance may offer advantages with respect to the ease of manufacturing and formulation of the drug.

Figure 3:
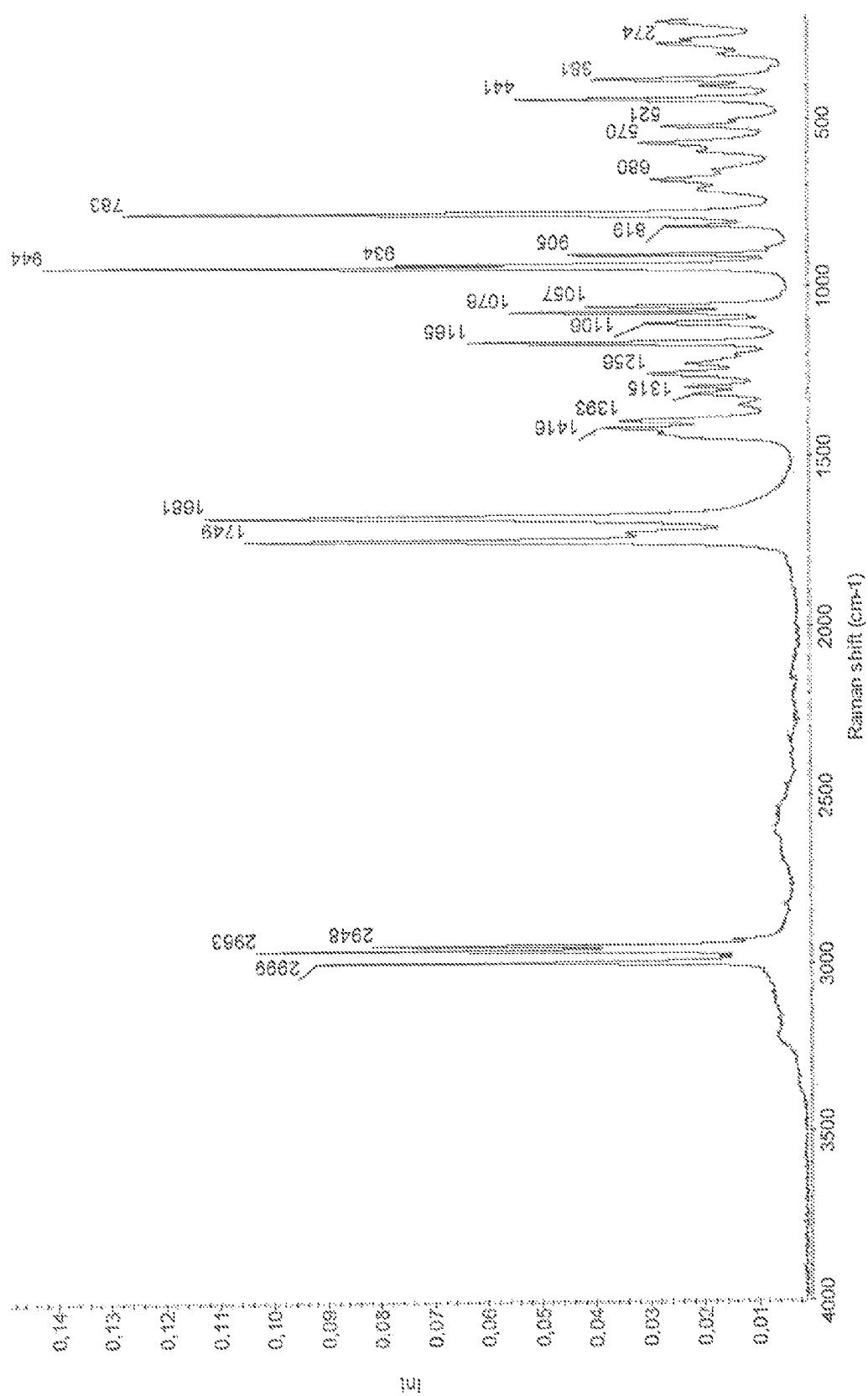

This citric acid cocrystal of N-[2-(7-methoxy-1-naphthyl)ethyl]acetamide is also characterized by the Raman spectrum given in FIG. 3. which shows characteristic peaks at approximately 2999, 2963, 2948, 1749, 1681, 1416, 1393, 1315, 1256, 1165, 1106, 1076, 944, 934, 905, 819, 783, 680, 570, 521, 441, 381 and 274 $cm^{-1}$.

In the manufacture of a solid oral dosage form it is of critical importance that the drug is manufactured and administered as a defined and consistent crystalline form (ICH, Q6A: Test Procedures and Acceptance Criteria for New Drug Products) in order to ensure that the bioavailability, stability and mechanical properties of the drug remain consistent throughout manufacture.

The crystallisation of the citric acid cocrystal of N-[2-(7-methoxy-1-naphthyl)ethyl]acetamide as described in Examples 1,2 and 3 demonstrates its propensity to crystallise as a consistent and pure crystalline phase. Additionally, the high melting point and thermal stability of the cocrystal enables drying procedures to be carried out with minimal precautions.

Figure 5:
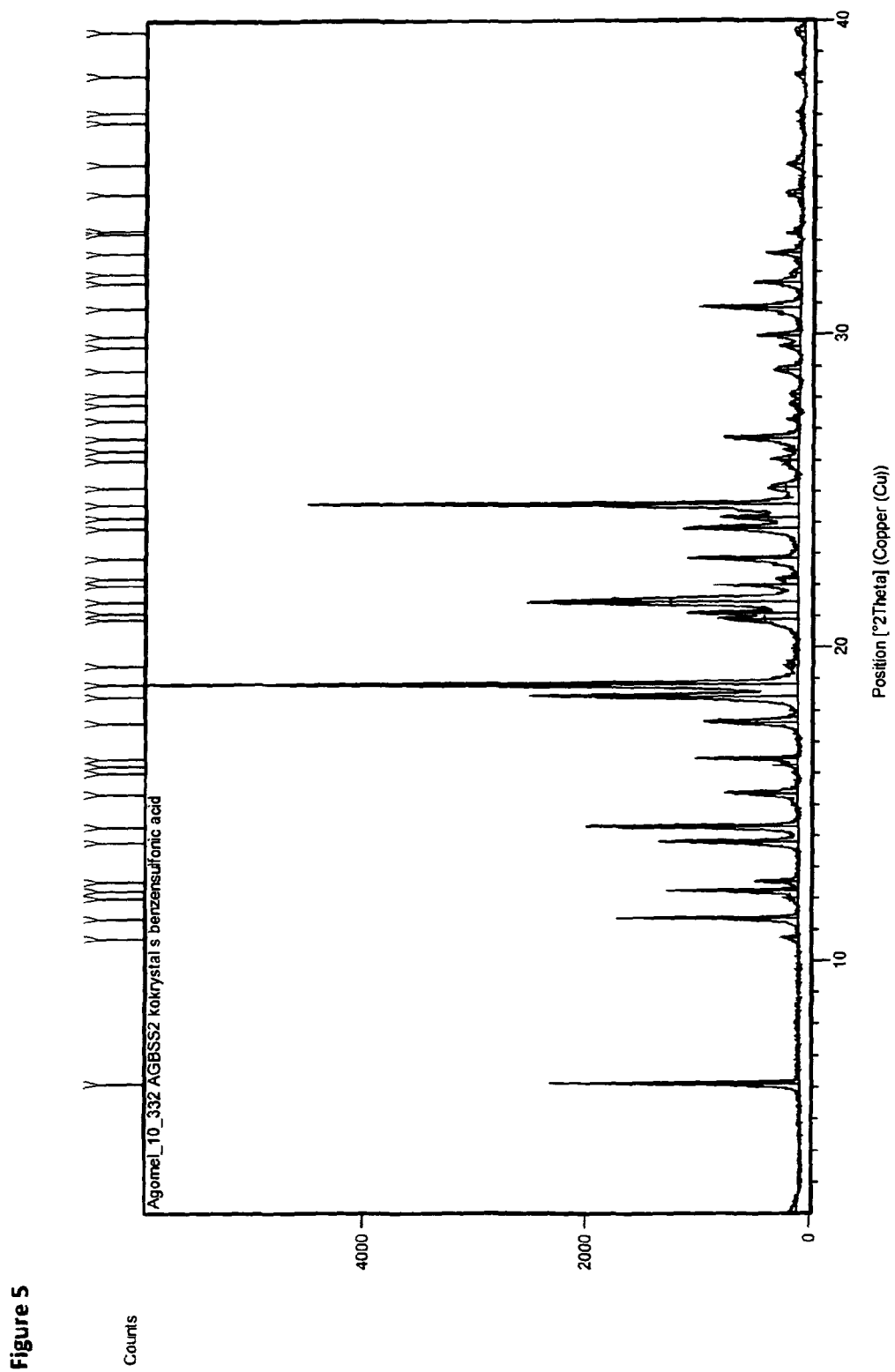

Benzenesulfonic acid cocrystal of N-[2-(7-Methoxy-1-naphthyl)ethyl]acetamide having the empirical formula $C_{15}H_{17}NO_2.C_6H_6SO_3$ is characterized by the XRPD pattern given in FIG. 5 with the main peaks listed in Table 2.

TABLE 2

Table of diffraction peaks for agomelatin cocrystal with benzenesulfonic acid.

| Diffraction angle (°2θ) | d-spacing [Å] | Relative intensity (%) |
|---|---|---|
| 6.11 | 14.454 | 35.8 |
| 11.37 | 7.779 | 26.5 |
| 12.23 | 7.229 | 18.3 |
| 13.79 | 6.418 | 22.0 |
| 14.27 | 6.200 | 31.0 |
| 15.33 | 5.774 | 9.9 |
| 16.45 | 5.386 | 15.4 |
| 17.61 | 5.031 | 14.2 |
| 18.45 | 4.806 | 42.8 |
| 18.83 | 4.709 | 100.0 |
| 20.90 | 4.246 | 11.6 |
| 21.11 | 4.206 | 15.5 |
| 21.47 | 4.136 | 44.0 |
| 22.85 | 3.890 | 16.0 |
| 23.81 | 3.734 | 18.4 |
| 24.17 | 3.680 | 10.8 |
| 24.58 | 3.619 | 71.5 |
| 26.69 | 3.338 | 12.0 |
| 28.86 | 3.091 | 4.4 |
| 29.62 | 3.014 | 2.9 |
| 30.85 | 2.896 | 12.0 |
| 31.65 | 2.825 | 6.8 |
| 32.59 | 2.745 | 5.6 |

Figure 6:
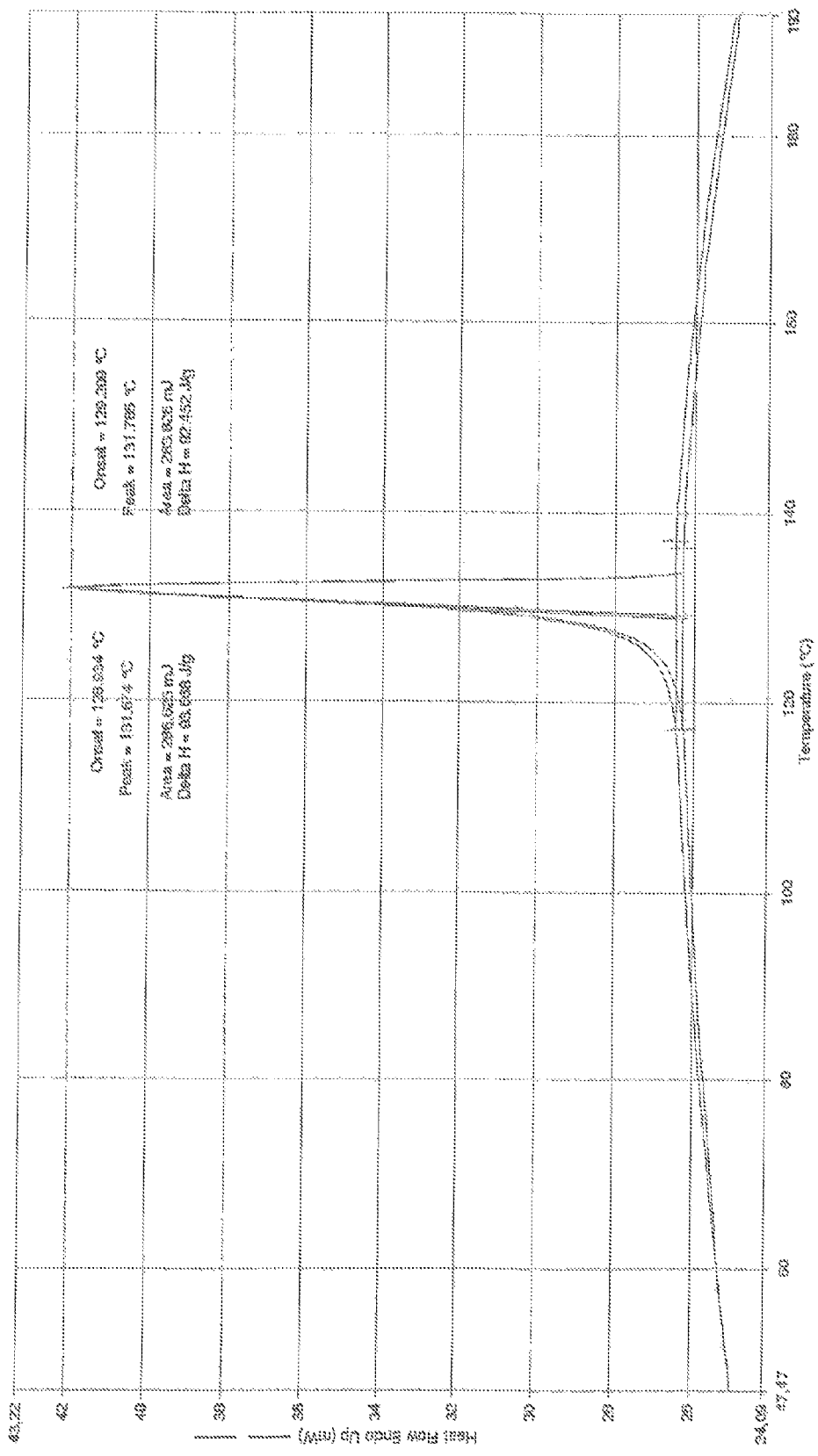

This benzenesulfonic acid cocrystal of N-[2-(7-methoxy-1-naphthyl)ethyl]acetamide is further characterized by the differential scanning calorimetry (DSC) thermograph shown in FIG. 6 which shows an endothermic event corresponding to a melt with an onset temperature of approximately 128° C.

Figure 7:
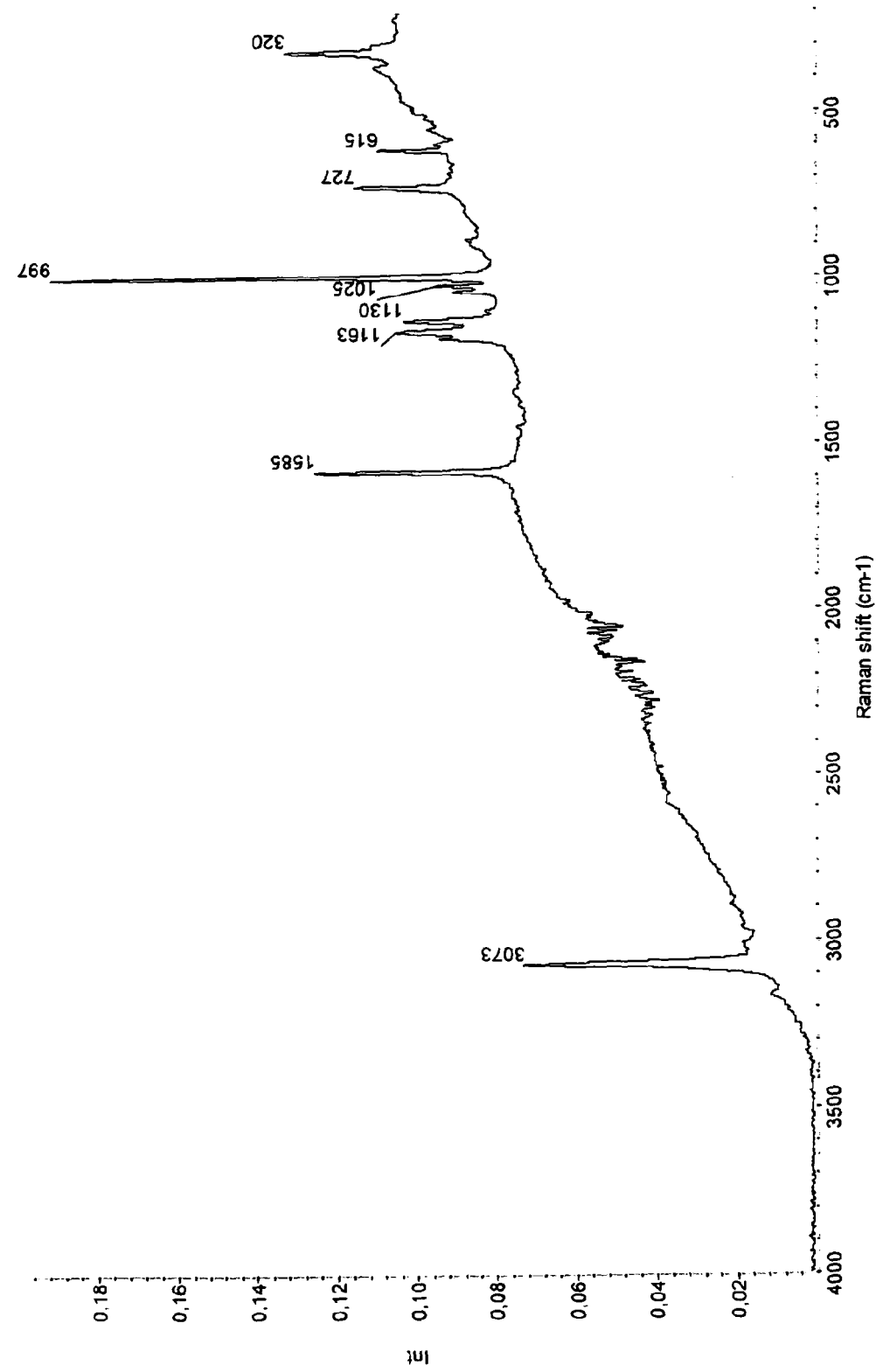

This benzenesulfonic acid cocrystal of N-[2-(7-Methoxy-1-naphthyl)ethyl]acetamide is also characterized by the Raman spectrum given in FIG. 7 which shows characteristic peaks at approximately 3073, 1585, 1163, 1130, 1025, 997, 727, 615 and 320 $cm^{-1}$.

Figure 8:
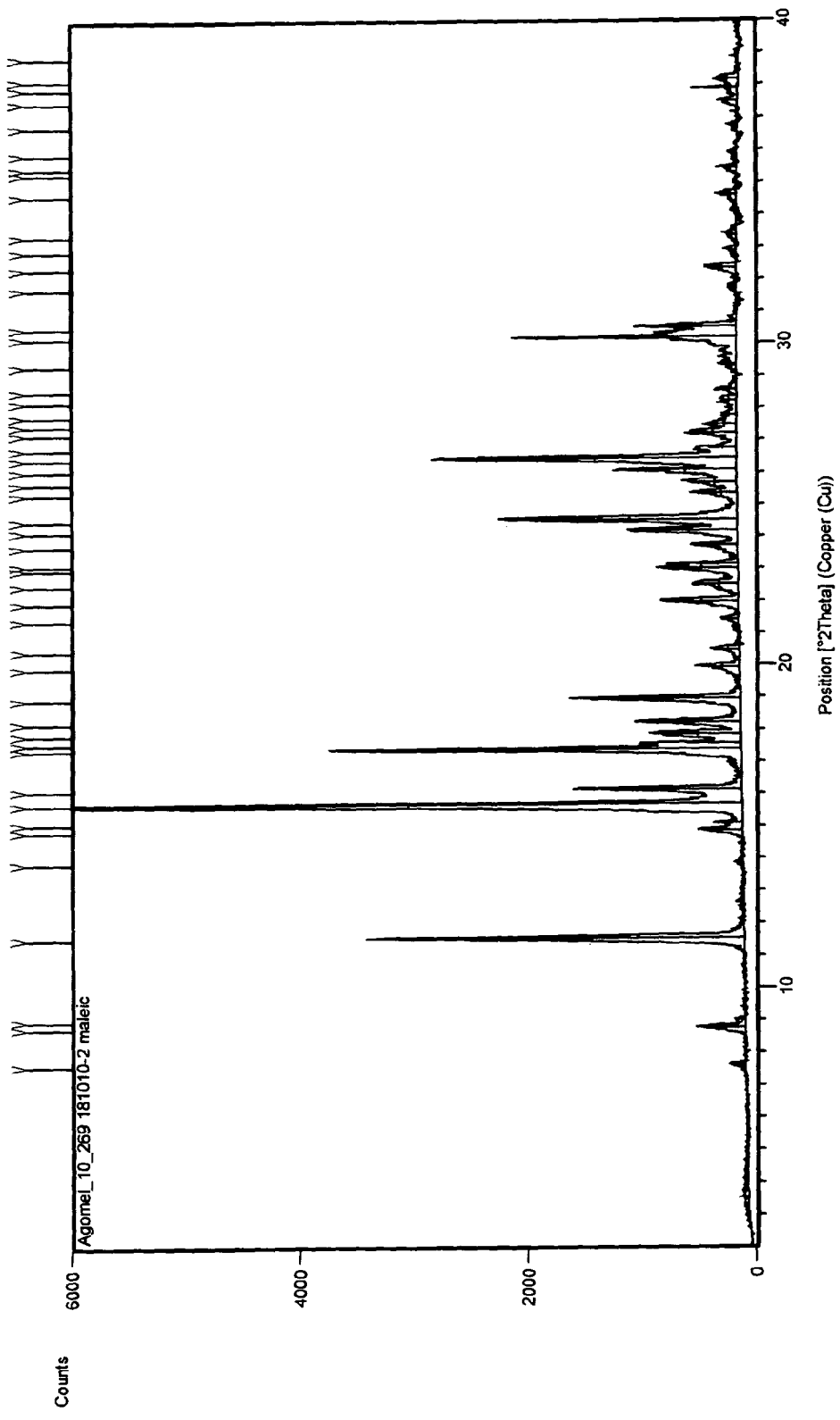

Maleic acid cocrystal of N-[2-(7-Methoxy-1-naphthyl)ethyl]acetamide having the empirical formula $C_{15}H_{17}NO_2.C_4H_4O_4$ is characterized by the XRPD pattern given in FIG. 8 with the main peaks listed in Table 3.

TABLE 3

| Diffraction angle (°2θ) | d-spacing [Å] | Relative intensity (%) |
|---|---|---|
| 8.76 | 10.081 | 6.2 |
| 11.53 | 7.667 | 50.5 |
| 15.69 | 5.645 | 100.0 |
| 16.14 | 5.486 | 20.2 |
| 17.39 | 5.095 | 53.3 |
| 17.86 | 4.962 | 11.9 |
| 18.23 | 4.863 | 13.4 |
| 18.96 | 4.678 | 23.4 |
| 19.93 | 4.450 | 5.0 |
| 21.97 | 4.042 | 10.3 |
| 22.51 | 3.947 | 5.3 |
| 23.01 | 3.861 | 10.2 |
| 23.71 | 3.749 | 6.3 |
| 24.18 | 3.678 | 13.6 |
| 24.54 | 3.625 | 30.2 |
| 26.05 | 3.417 | 14.3 |
| 26.42 | 3.371 | 39.5 |
| 27.22 | 3.274 | 6.5 |
| 30.18 | 2.959 | 19.5 |
| 32.34 | 2.766 | 4.1 |

Figure 9:
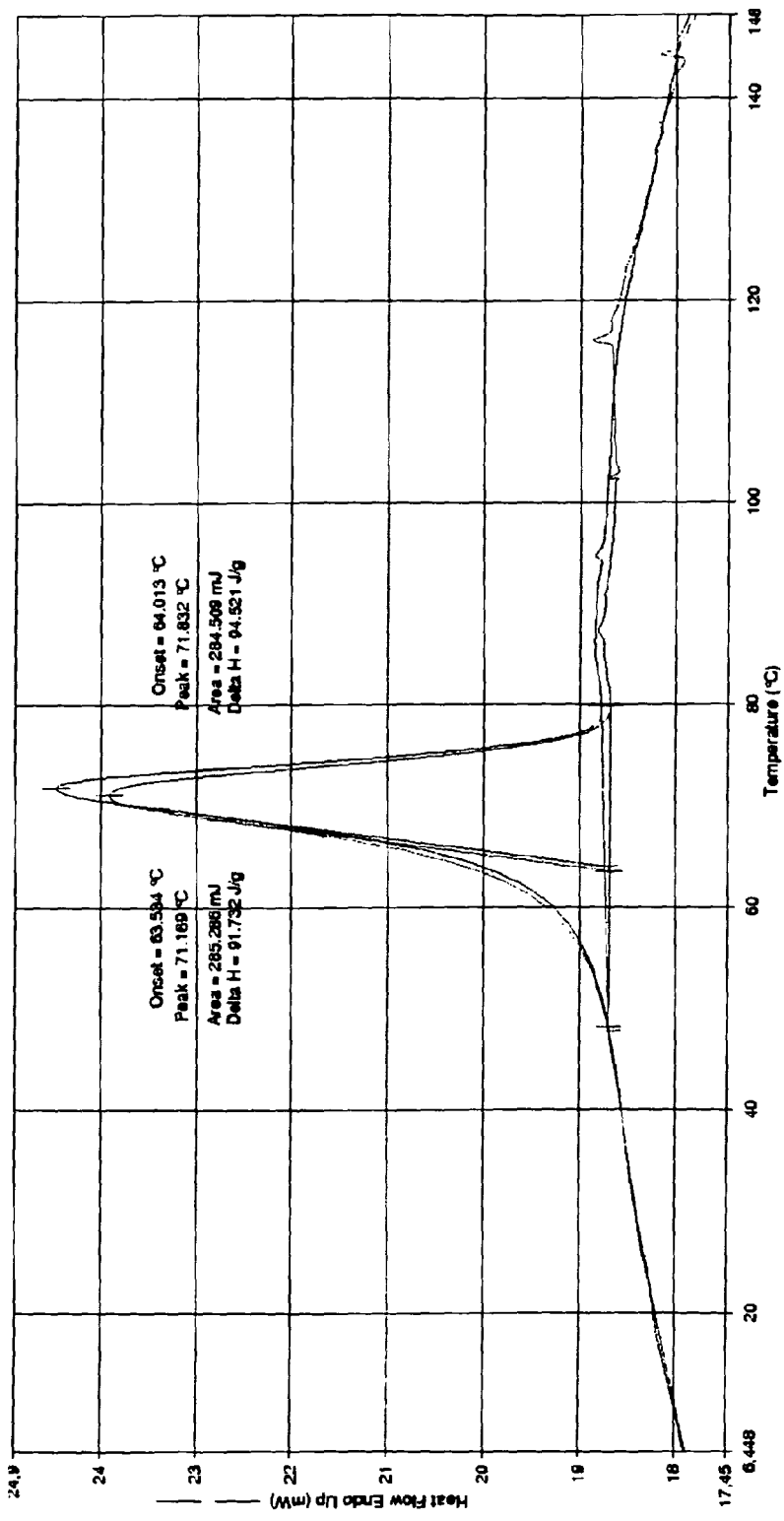

This maleic acid cocrystal of N-[2-(7-Methoxy-1-naphthyl)ethyl]acetamide is further characterized by the differential scanning calorimetry (DSC) thermograph shown in FIG. 9. which shows an endothermic event corresponding to a melt with an onset temperature of approximately 64° C.

Figure 10:
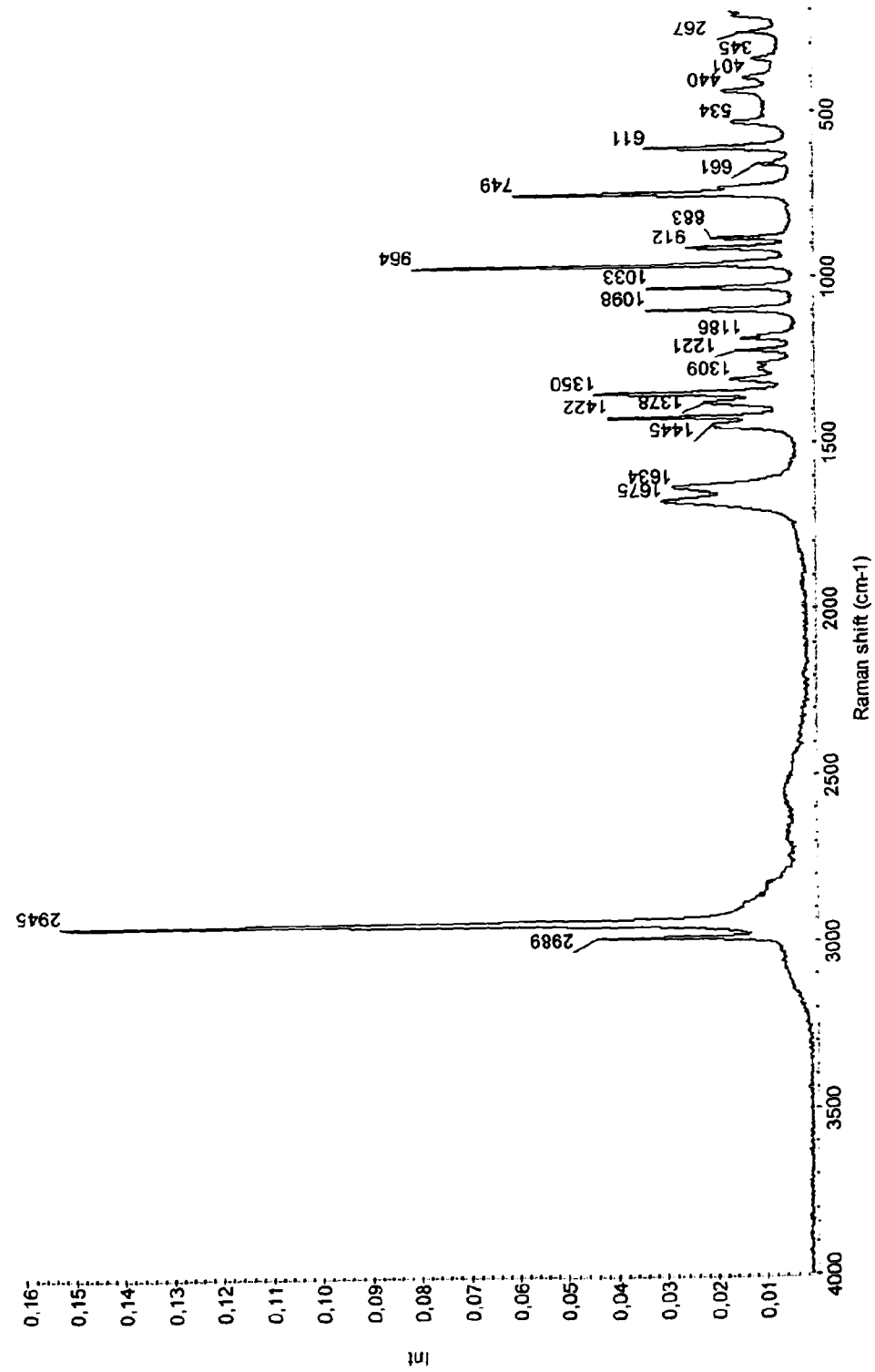

This maleic acid cocrystal of N-[2-(7-Methoxy-1-naphthyl)ethyl]acetamide is also characterized by the Raman spectrum given in FIG. 10, which shows characteristic peaks at 2989, 2945, 1675, 1634, 1445, 1422, 1378, 1350, 1309, 1221, 1186, 1098, 1033, 964, 912, 883, 794, 661, 611, 534, 440, 401, 345 and 267 $cm^{-1}$.

XRPD patterns were measured with laboratory X-Ray diffractometer X'PERT PRO MPD PANalytical operating in diffraction mode θ-θ with copper radiation CuKα (λ=1.542 Å, 45 kV/40 mA), graphite monochromator, in 2theta range 2-40° 2θ, with step size 0.01° 2θ and time per step 50 s. Primary optics setting: Soller slits 0.02 rad, automatic PDS, 10 mm mask, 1/4° anti-scatter slit, irradiated sample area 10 mm. Secondary optics setting: 5.0 mm anti-scatter slit, Soller slits 0.02 rad, detector X'Celerator with maximal active length. Samples were measured on a silica plate holder.

All the DSC thermographs reported herein were acquired with a scanning rate of 10° C./min.

The cocrystals according to the invention can be prepared by dissolving agomelatine with the cocrystal former in a proper solvent or solvent mixture and cooling the resulting solution or allowing the solvent to evaporate. The latter method was particularly useful for obtaining a first batch of crystalline material, which can be used for seeding in subsequent batches. The addition of an amount of a seed crystal is the preferred but not the sole method for inducing crystallization of the cocrystals according to the invention on an industrial scale. The induction of crystallisation using ultrasound was also successfully employed.

In a preferred procedure, agomelatine is dissolved in a solvent which can be preferably selected from the C3-C8 ketones such as acetone, butanone, cyclohexanone or acetofenone, C1-C8 alcohols or ether-alcohols like methanol, ethanol, 1- or 2-propanol, 1-butanol, 2-butanol, isobutyl alcohol, 2-methyl-2-propanol, amyl alcohol, cyclohexanol, benzyl alcohol, 2-methoxyethanol or tetrahydrofurfuryl alcohol, cyclic C5-C6 ethers like tetrahydrofuran, methyltetrahydrofuran or dioxan, C3-C8 esters like ethyl acetate or butyl acetate, C2-C8 nitriles such as acetonitrile, propionitrile or benzonitrile and mixed with a solution of the chosen cocrystal former in the same or different solvent as the solvent used for agomelatine, which solvent can be preferably selected from C1-C5 alcohols or ether-alcohols like above, water and mixtures of C1-C5 alcohols or ether-alcohols with water. Preferably the mixing proceeds at the temperature between 20° C. and reflux temperature of the resulting mixture, most preferably in the temperature range between the temperature which is 25 K lower than the boiling point of the resulting mixture and the boiling point of the resulting mixture. The resulting mixture can be directly cooled to the temperature between the mixing temperature and melting point of the solvent or solvent mixture, or partially evaporated and then cooled. The preferred crystallization temperature is between −5° C. and 15° C., the most preferable range being 0-5° C. Optionally, the crystallization can be induced by the addition of an antisolvent to the crystallization mixture, preferably after the cooling to the chosen crystallization temperature and/or seeding. The preferred antisolvents are C4-C8 aliphatic ethers like diethyl ether, methyl-tert-butyl ether, diisopropylether or anisole, and C6-C10 hydrocarbons like cyclohexane, methylcyclohexane, toluene or tetrahydronaphthalene.

LIST OF DRAWINGS

FIG. 1: N-[2-(7-Methoxy-1-naphthyl)ethyl]acetamide citric acid cocrystal XRPD pattern.

Figure 1A:
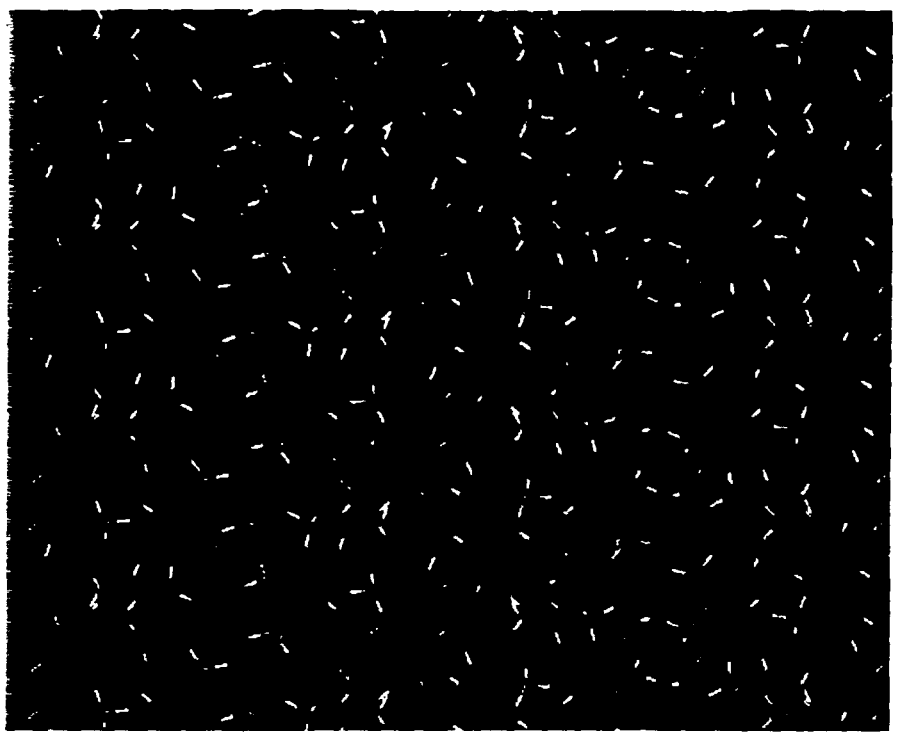
Figure 1A:
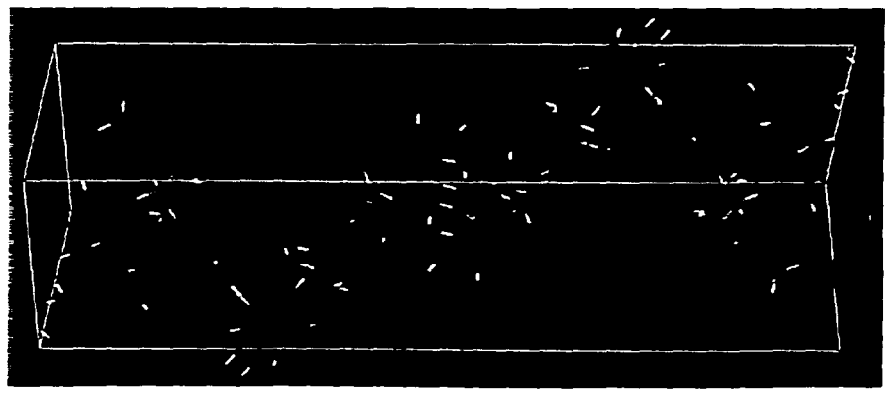
Figure 1B:
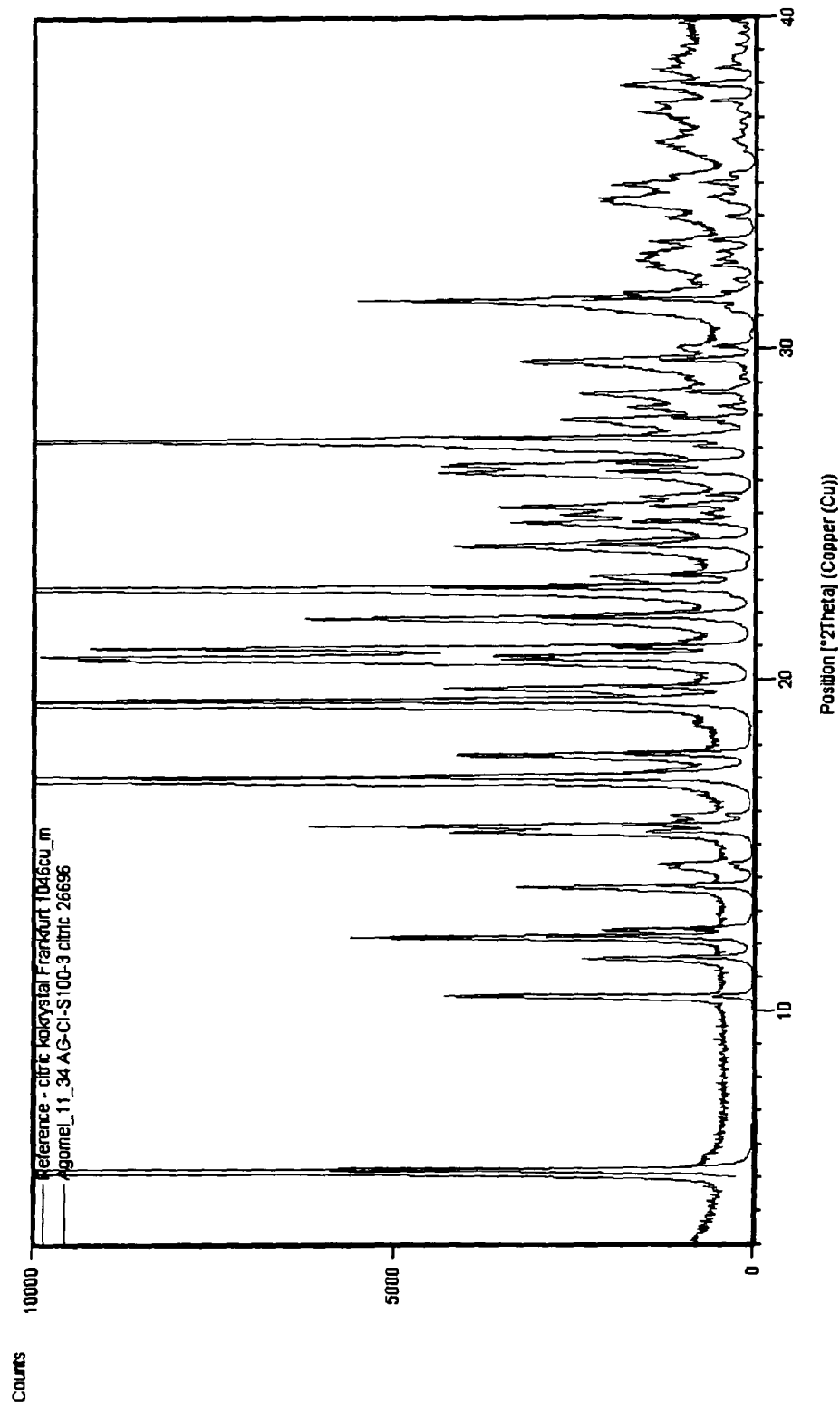

FIG. 1a: Crystal structure of N-[2-(7-methoxy-1-naphthyl)ethyl]acetamide citric acid cocrystal obtained by SXRD. Unit cell (left), packing arrangement (right).

FIG. 1b: Comparison of the XRPD pattern calculated from the SXRD structure and the experimental XRPD pattern.

FIG. 2: N-[2-(7-Methoxy-1-naphthyl)ethyl]acetamide citric acid cocrystal DSC.

FIG. 3: N-[2-(7-Methoxy-1-naphthyl)ethyl]acetamide citric acid cocrystal Raman spectrum.

Figure 4:
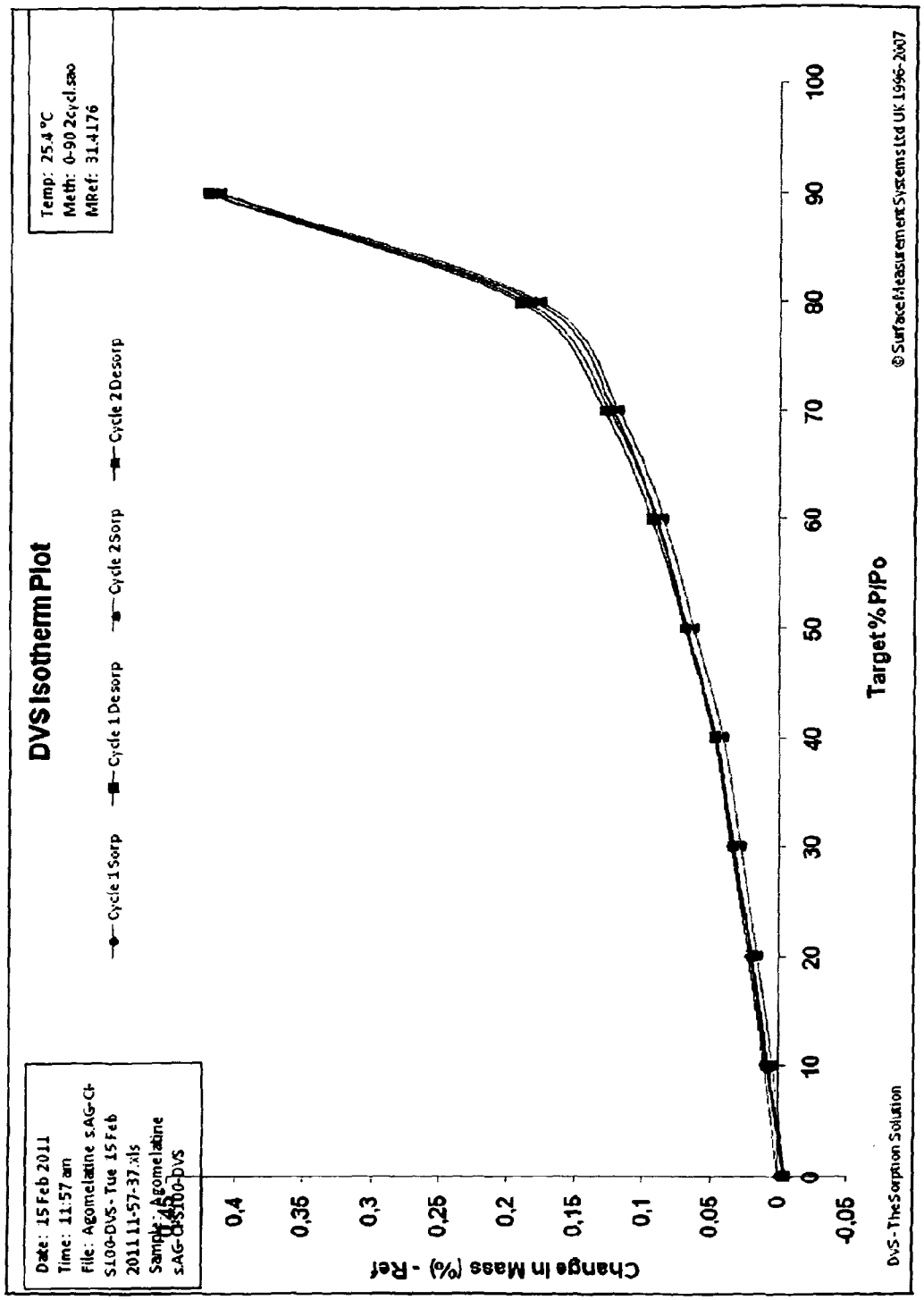

FIG. 4: DVS Isotherm plot for agomelatine citric acid cocrystal

FIG. 5: N-[2-(7-Methoxy-1-naphthyl)ethyl]acetamide benzenesulfonic acid cocrystal XRPD pattern.

FIG. 6: N-[2-(7-Methoxy-1-naphthyl)ethyl]acetamide benzenesulfonic acid cocrystal DSC.

FIG. 7: N-[2-(7-Methoxy-1-naphthyl)ethyl]acetamide benzenesulfonic acid cocrystal Raman spectrum.

FIG. 8: N-[2-(7-Methoxy-1-naphthyl)ethyl]acetamide maleic acid cocrystal XRPD pattern.

FIG. 9: N-[2-(7-Methoxy-1-naphthyl)ethyl]acetamide maleic acid cocrystal DSC.

FIG. 10: N-[2-(7-Methoxy-1-naphthyl)ethyl]acetamide maleic acid cocrystal Raman spectrum. Representative examples of the preparations of the compounds of the invention are given below. The given examples do not limit the scope of the invention.

EXAMPLES

Example 1

General Procedure for the Preparation of N-[2-(7-methoxy-1-naphthyl)ethyl]acetamide Cocrystals 500 mg of N-[2-(7-methoxy-1-naphthyl)ethyl]acetamide was dissolved in 5 ml of methanol at ambient temperature and one stoichiometric equivalent of the cocrystal former selected from citric, benzenesulfonic or maleic acid was added as a solution in methanol. The solution was heated to a temperature between ambient and reflux to ensure complete dissolution and the solvent was allowed to evaporate at room temperature to crystallize the cocrystals of N-[2-(7-Methoxy-1-naphthyl)ethyl]acetamide with the cocrystal former.

Example 2

Preparation of N-[2-(7-methoxy-1-naphthyl)ethyl]acetamide Citric Acid Cocrystal (Method A)

100 g N-[2-(7-Methoxy-1-naphthyl)ethyl]acetamide was slurried in 400 ml ethyl acetate at room temperature and heated to reflux to dissolve the entire solid. The solution was cooled to 60° C. and a solution of 78.9 g anhydrous citric acid dissolved in 300 ml methanol was added. The solution was concentrated by distillation to approximately half its volume then cooled to a temperature in the range 2-5° C. and 140 mg of seed crystals prepared by evaporation of a methanolic solution of agomelatine and citric acid were added. Precipitation was observed and a thick white slurry was formed during stirring for 1 hour. The white solid was isolated by filtration and washed with 100 ml ethyl acetate, the final yield of dry material was 97 g (54%) and the purity of agomelatin in the solid was 99.6% with no impurities above 0.4% by UPLC. The isolated solid gave the XRPD pattern shown in FIG. 1, the DSC thermograph shown in FIG. 2 with an onset of melting of approximately 123.5° C. and the Raman spectrum shown in FIG. 3.

Example 3

Preparation of N-[2-(7-methoxy-1-naphthyl)ethyl]acetamide Citric Acid Cocrystal (Method B)

100 g N-[2-(7-methoxy-1-naphthyl)ethyl]acetamide was dissolved in 240ml acetone at 60° C. to give a clear yellow solution. A suspension of 78.9 g citric acid in 300 ml acetone at 40° C. was added to give a clear yellow solution. The solution was concentrated to approximately half its original volume and cooled to approximately 2-5° C. An approximately 2 ml fraction was removed and placed in an ultrasonic bath to induce crystallisation. The cloudy fraction was returned to the mother solution and over 1 hour crystallisation occurred to give a white suspension. The suspension was maturated by stirring at ambient temperature for 48 hours and the white solid was isolated by filtration and washed with cold diethyl ether then dried at 40° C. at a pressure of 150 mbar for 20 hours. The final yield of dry material was 148 g (83%) and the purity of agomelatin in the solid was 99.9% with no impurities above 0.1% by UPLC. The isolated white solid (small bladed crystals) gave an XRPD pattern consistent with that shown in FIG. 1 and a DSC thermograph consistent with that shown in FIG. 2 with an onset of melting of approximately 123.5° C.

Example 4

Stability of N-[2-(7-methoxy-1-naphthyl)ethyl]acetamide Citric Acid Cocrystal in Suspension Samples of the agomelatine citric acid cocrystal were maturated as suspensions in a library of organic solvents including alcohols, ketones, esters, alkanes and aromatic hydrocarbons at a temperature of 30° C. for one week. Analysis of the recovered solids by Raman spectroscopy indicated that the crystalline phase is generally stable for a range of solution environments.

Example 5

Thermal Stability of N-[2-(7-methoxy-1-naphthyl)ethyl]acetamide Citric Acid Cocrystal A sample of the agomelatine citric acid cocrystal was heated to 90° C. in a glass capillary for 7 hours. Analysis of the recovered solid by X-ray powder diffraction showed a pure crystalline phase consistent with the agomelatine citric acid cocrystal.

Example 6

Hygroscopicity and Moisture Stability of N-[2-(7-methoxy-1-naphthyl)ethyl]acetamide Citric Acid Cocrystal A sample of the agomelatine citric acid cocrystal was subjected to DVS analysis (Differential Vapor Sorption). The sample was placed on a microbalance in a controlled humidity chamber and subjected to two cycles of increasing humidity (red and green lines) and two cycles of decreasing humidity (blue and purple lines) as shown in FIG. 4. It can be seen that the sample is not particularly hygroscopic in the range of 20-80% RH as the change in mass is less than 0.2%.

Example 7

Rate of Liberation of Agomelatine Into Solution From Citric Acid Cocrystal

A sample of the agomelatine citric acid cocrystal was slurried in water and the solid analysed by Raman spectroscopy at 20 minute intervals. Immediately upon addition to the water the bands corresponding to the citric acid component of the cocrystal indicated that the citric acid was dissolving into water whilst the bands corresponding to the agomelatine component indicated a change in the crystalline phase present. After 20 minutes the Raman spectra indicated near to complete dissolution of the citric acid with the solid phase of the agomelatine component still changing. After 40 minutes no further changes in the spectrum were observed indicating that free agomelatine had stabilized in the slurry.

Example 8

Preparation of N-[2-(7-methoxy-1-naphthyl)ethyl]acetamide Benzenesulfonic Acid Cocrystal 1 g of N-[2-(7-methoxy-1-naphthyl)ethyl]acetamide was dissolved in 15 ml ethyl acetate at room temperature and a solution of 0.78 g of benzenesulfonic acid in 1 ml of methanol was added. The immediate formation of small crystals was observed, the solution was cooled to 2° C. and 5 ml of cyclohexane was added as an antisolvent to improve the yield. The crystalline product (slightly brown tabular crystals) was isolated by filtration. The isolated solid gave the XRPD pattern shown in shown in FIG. 5, the DSC thermograph shown in FIG. 6 with an onset of melting of approximately 128.5° C. and the Raman spectrum shown in FIG. 7.

Example 9

Preparation of N-[2-(7-methoxy-1-naphthyl)ethyl]acetamide Maleic Acid Cocrystal 1 g of N-[2-(7-Methoxy-1-naphthyl)ethyl]acetamide was dissolved in 15 ml ethyl acetate at room temperature and a solution of 0.574 g of maleic acid in 2 ml of methanol was added. The solution was slowly concentrated to yield a yellow oil that crystallized over one week. The isolated solid (off-white microcrystals) gave the XRPD pattern shown in FIG. 8, the DSC thermograph shown in FIG. 9 with an onset of melting of approximately 65.5° C. and the Raman spectrum shown in FIG. 10.

The invention claimed is:

1. A cocrystal of N-[2-(7-methoxy-1-naphthyl)ethyl]acetamide (agomelatine) with a cocrystal former selected from the group consisting of citric acid and benzenesulfonic acid.

2. The cocrystal according to claim 1, wherein the cocrystal former is citric acid, characterised by one or more of the following features:
   i) an X-ray powder diffraction (XRPD) pattern with main peaks at 2-theta values of 5.2; 12.2; 17.0; 19.3; 20.6; 22.7 and 27.3±0.2°;
   ii) a melting point in the range of 123-127° C.; and iii) Raman scattering peaks at wave numbers 2963, 1749, 1681, 944, 783 cm$^{-1}$.

3. The cocrystal according to claim 1, wherein the cocrystal former is benzenesulfonic acid, characterised by one or more of the following features:
   i) an X-ray powder diffraction (XRPD) pattern with main peaks at 2-theta values of 11.5, 15.7, 17.4, 19.0, 24.5 and 26.4±0.2°;
   ii) a melting point in the range of 128-132° C.; and
   iii) Raman scattering peaks at wave numbers 3073, 1585, 1163, 997, 727 cm$^{-1}$.

4. A process for preparing a cocrystal as described in claim 1 comprising the steps of dissolving N-[2(7-methoxy-1-naphthyl)ethyl]acetamide in a solvent selected from the C3-C8 ketones, C1-C8 alcohols or ether-alcohols, cyclic C5-C6 ethers, C3-C8 esters, C2-C8 nitrile or mixture thereof, with a cocrystal former to form a cocrystal; and
   crystallizing the cocrystal by cooling the solution or allowing the solvent to evaporate.

5. The process according to claim 4 wherein a cocrystal is added to the solution as a seed.

\* \* \* \* \*